United States Patent
Rey

(10) Patent No.: US 8,375,780 B2
(45) Date of Patent: Feb. 19, 2013

(54) TRACTION PAD FOR DEVICE TESTING ADHESION OF A COATING ON A SUBSTRATE

(75) Inventor: Stephane Rey, Lavernose Lacasse (FR)

(73) Assignee: Airbus Operations SAS, Toulouse (FR)

( * ) Notice: Subject to any disclaimer, the term of this patent is extended or adjusted under 35 U.S.C. 154(b) by 624 days.

(21) Appl. No.: 12/088,050

(22) PCT Filed: Sep. 27, 2006

(86) PCT No.: PCT/EP2006/066803
§ 371 (c)(1),
(2), (4) Date: Sep. 2, 2008

(87) PCT Pub. No.: WO2007/036541
PCT Pub. Date: Apr. 5, 2007

(65) Prior Publication Data
US 2009/0126474 A1 May 21, 2009

(30) Foreign Application Priority Data
Sep. 28, 2005 (FR) ...................................... 05 52936

(51) Int. Cl.
*G01N 19/04* (2006.01)
(52) U.S. Cl. ........................... 73/150 A; 73/827; 73/842
(58) Field of Classification Search .................. 73/9, 10, 73/150 R, 827, 842, 150 A
See application file for complete search history.

(56) References Cited

U.S. PATENT DOCUMENTS

| | | | | |
|---|---|---|---|---|
| 2,008,952 A | * | 7/1935 | Gach | 15/245.1 |
| 2,113,725 A | * | 4/1938 | Goldman | 73/150 A |
| 3,043,129 A | * | 7/1962 | King | 73/40 |
| 3,336,797 A | * | 8/1967 | Raffalovich | 73/150 A |
| 3,527,093 A | * | 9/1970 | Sellers | 73/150 R |
| 3,585,856 A | * | 6/1971 | Schaeffer | 73/150 R |
| 3,821,892 A | | 7/1974 | Saberg | |
| 4,393,699 A | * | 7/1983 | Seiler, Jr. | 73/150 A |
| 4,476,727 A | * | 10/1984 | Hawk et al. | 73/847 |
| 4,491,014 A | * | 1/1985 | Seiler, Jr. | 73/150 A |
| 4,501,154 A | * | 2/1985 | Mori | 73/827 |
| 4,567,758 A | * | 2/1986 | Fisher et al. | 73/150 A |
| 4,606,225 A | | 8/1986 | Thomason et al. | |
| 4,876,896 A | * | 10/1989 | Snow et al. | 73/827 |
| 5,313,841 A | * | 5/1994 | Layher | 73/827 |
| 5,337,614 A | * | 8/1994 | Jiang et al. | 73/827 |
| D363,880 S | * | 11/1995 | Liebmann | D9/456 |
| 5,671,634 A | * | 9/1997 | Donovan | 73/150 A |
| 5,749,498 A | * | 5/1998 | Lavoie et al. | 222/192 |
| 5,976,292 A | * | 11/1999 | Barksdale et al. | 156/157 |
| 6,050,140 A | | 4/2000 | Koch et al. | |

(Continued)

FOREIGN PATENT DOCUMENTS

| | | | |
|---|---|---|---|
| DE | 10250390 A1 | * | 5/2004 |
| EP | 0433512 A1 | | 6/1991 |

(Continued)

*Primary Examiner* — David Rogers
(74) *Attorney, Agent, or Firm* — Perman & Green LLP

(57) ABSTRACT

The disclosed embodiments concerns a traction pad to be bonded for coating adhesion or surface cohesion tests by tearing including a counterbore designed to control the thickness of the adhesive film. Support elements such as wedges or a border maintain the base of the counterbore at the required distance from the tested surface and openings are provided for evacuating the adhesive prior to its controlled hardening when the traction pad is applied on the tested surface.

11 Claims, 3 Drawing Sheets

U.S. PATENT DOCUMENTS

| | | | | |
|---|---|---|---|---|
| 6,129,666 | A * | 10/2000 | DeLuca et al. | 600/372 |
| 6,237,422 | B1 * | 5/2001 | Sykes | 73/859 |
| 6,308,370 | B1 * | 10/2001 | Southby | 15/245.1 |
| 6,324,916 | B1 * | 12/2001 | Jessop | 73/842 |
| 6,428,233 | B1 * | 8/2002 | Clark et al. | 401/196 |
| 6,553,843 | B1 * | 4/2003 | Courtade | 73/827 |
| 6,976,396 | B2 * | 12/2005 | Roe et al. | 73/856 |
| 7,736,452 | B2 * | 6/2010 | McBroom | 156/64 |
| 2001/0031170 | A1 * | 10/2001 | Voiers et al. | 401/196 |
| 2005/0000941 | A1 * | 1/2005 | Ward | 216/83 |
| 2009/0298395 | A1 * | 12/2009 | Ward | 451/41 |

FOREIGN PATENT DOCUMENTS

| | | | |
|---|---|---|---|
| GB | 2130283 | A * | 5/1984 |
| GB | 2196437 | A | 4/1988 |
| JP | 03295290 | A * | 12/1991 |
| JP | 2005129668 | A * | 5/2005 |

* cited by examiner

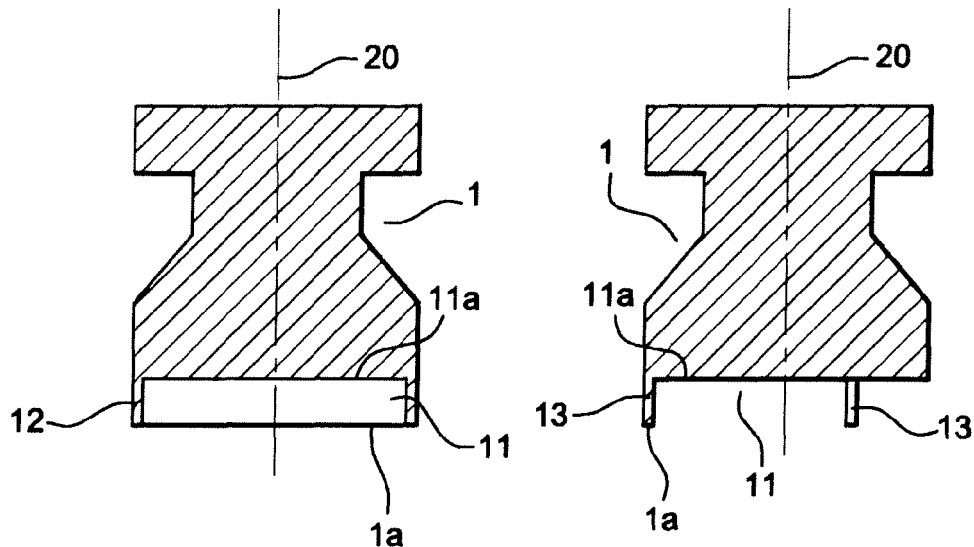
Fig. 4a          Fig. 5a
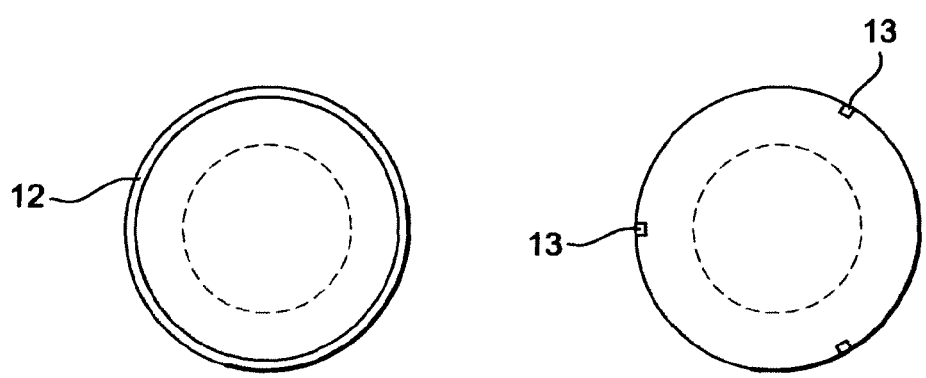
Fig. 4b          Fig. 5b

TRACTION PAD FOR DEVICE TESTING ADHESION OF A COATING ON A SUBSTRATE

CROSS-REFERENCE TO RELATED APPLICATIONS

This application is the National Stage of International Application No. PCT/EP2006/066803, International Filing Date, Sep. 27, 2006, which designated the United States of America, and which international application was published under PCT Article 21(2) as WO Publication No. WO 2007/036541 A1 and which claims priority from French Application No. 05 52936, filed Sep. 28, 2005, the disclosures of each being incorporated by reference in their entirety.

BACKGROUND

1. Field

The disclosed embodiments relate to devices used for measuring the adhesion qualities of coatings such as paints, surface protections, adhesive or adhesive films on substrates which they are intended to, or measuring the surface cohesion qualities in general.

More particularly, the disclosed embodiments relate to an improvement of traction pads used by such devices and which are bonded on the surface, the adhesion performances of which are to be measured by exerting a tearing force through said traction pads.

2. Brief Description of Related Developments

Knowing the adhesion qualities of a coating on a substrate, for example paint on its intended support, or the cohesion of the surface of a material, is essential data in industry since the behaviour of parts and assemblies of such parts in their future operating environments greatly depends thereon.

A currently used method for determining such adhesion qualities of a coating or surface cohesion consists in measuring the efforts required for causing the tearing of a sample of the substrate coating on a test-portion, which it has been deposited on, or parts of the surface of the material.

Tests are often carried out on standardised test-portions and follow precisely defined protocols, since being able to reproduce the measures repeatedly in order to be able to have an efficient comparison of the adhesion performances of the various pairs coating-substrate is very useful.

The general principle of such a measurement consists in bonding a rigid pad of the calibrated bonding surface on a sample of the surface to be estimated, i.e. a substrate coated with a coating according to the planned application method or a sample of a material having been exposed to surface treatments and, when the adhesive has set, in applying a traction on the pad until it is torn from the coating of the surface of the substrate or of the surface material.

The force corresponding to such tearing gives us a measure of the qualities of adhesion or cohesion desired.

The standard ISO 4624 describes the procedure to be implemented so that the results obtained by various testing laboratories can be compared.

Tractions devices such as the one described in patent U.S. Pat. No. 3,821,892 can also be found, which are implemented to carry out the tests mentioned.

The described device makes it possible to exert a traction force on a bobbin-shaped bonded pad, and is provided with means for measuring the traction effort applied.

However, although it is clear that the pad is bonded on the tested surface, the standard only mentions that the bonded surface of the pad must be flat. Thus, in the standard ISO 4624, as well as in patent U.S. Pat. No. 3,821,892, nothing mentions that the surface for bonding the pad should be anything but plane, which is a shape which is explicitly requested. When the shape of the traction pad is mentioned, such as its bobbin shape in patent U.S. Pat. No. 3,821,892, the aim is just to provide a good gripping of the pad by the traction means.

Experience shows that the quality of the results obtained upon the implementation of the standard ISO 4624 is closely related to the quality of the bonding of the pad and to the quality of the test preparation. Most of the time, such qualities of preparation and bonding are not totally satisfactory, which results in an important perturbation of the measurements of the tearing forces.

First, because of the fluidity of the adhesive upon the bonding of the pad on the surface to be tested, it is very difficult to check the thickness of the adhesive film and in particular, to have a uniform thickness of such film between the lower surface of the pad and the surface tested. Because of a not-controlled thickness and of the possible side lowering of the pad, the orientation of the axis of the pad can be shifted with respect to the normal to the surface of the test portion, which is the traction direction on the pad during the test. In practice, a deviation, even a small one, of the axis of the pad with respect to the traction axis and a variation of the thickness of the adhesive film at the interface between the traction pad and the tested coating substantially affect the value of the force measured upon the tearing, and this effect is problematic, since it leads to a significant dispersion of measures.

To take this phenomenon in consideration, the test operator is generally obliged to multiply the tests and repeat them a lot of times to obtain average values of the tearing stresses which can be used.

Secondly, a curl of adhesive is formed around the pad upon the bonding of said pad. Such curl is composed of the fluid adhesive which is pushed laterally when the pad is pressed on the surface to be tested to provide a good adherence of the pad. The test procedure provides that the coating submitted to a tearing test is cut along the profile of the pad, so that the surface of the adhesion of the coating deposited on the substrate opposite the pad is taken into account in the measurement of the tearing stresses. A notch is thus cut in the coating around the pad, which requires the previous elimination of the curl of adhesive. Such curl of adhesive, which has hardened at this stage of the operations of the preparation of the test-portion, requires the application of important stresses on the pad itself to be eliminated. Frequently, during such operation of elimination of the adhesive curl, the applied efforts cause the pad to start ungluing, which makes the test portion inappropriate for carrying out the test, or give non-significant results of the test and thus, it is necessary to make a new test portion.

SUMMARY

It would be advantageous to solve such adhesion problems and the issues of the preparation of the test portion by choosing a pad having original characteristics, without such characteristics questioning the existing traction and measuring means, nor the test procedures used.

According to the disclosed embodiments, the traction pad for testing the coating adhesion on a substrate includes a reference axis and a lower surface, said traction pad being fixed on the surface of the coating prior to the test, using an adhesive. Said pad is characterised in that it further includes, on the lower surface intended to be bonded on the coating, a counterbore, the depth of which substantially corresponds to the thickness of the adhesive requested for fixing the traction pad to the coating and means for spacing the bottom of the counterbore, in order to provide the stability of the traction pad and holding its axis perpendicular to the plan defined by the surface of the coating to be tested, when the lower surface of the pad is applied onto the surface of the coating.

In a preferred embodiment, the counterbore has a substantially constant depth.

The spacing means are constituted by a border at the lower surface of a traction pad. Such border is preferably at the periphery of said lower surface.

In another embodiment, the spacing means are constituted by spacers distributed on the lower surface of the traction pad, on the perimeter of said lower surface. The lower surfaces of said wedges in contact with the surface of the coating to be tested constitute the support surface of the pad.

Whatever the shape of the embodiment of the pad, the spacing means can be obtained by leaving material from the traction pad when making the counterbore.

In one embodiment, the traction pad includes means capable of letting the adhesive in excess flux out of the bonding area defined by the mark of the traction pad on the surface of the coating. Thus, the adhesive in excess is evacuated out of the perimeter of the bonding of the plot without such means affecting the regularity of the thickness of the adhesive film. In a first alternative solution, such means are formed as free passages arranged in the border of the lower surface of the pad. In a second alternative embodiment, such means are arranged between the spacers. Finally, in a third alternative embodiment, such means consist in one or more exhaust stacks going up into the body of the traction pad. Preferably, at least one of said exhaust stacks opens onto the outer surface of the traction pad, in a part of said pad located above the bottom of the counterbore. At least one of the exhaust stacks can open onto an expansion chamber, in addition.

In the disclosed embodiments, the lower surface of the traction pad preferably includes surface unevenness. Such voluntarily created or voluntarily left unevenness improves the adhesion of the adhesive on the lower surface of the pad.

The disclosed embodiments also relate to a method for bonding a traction pad on a coating covering a substrate, using an adhesive and including the following steps:

a) applying the adhesive on the lower surface of the traction pad and/or on the surface of the coating;

b) prior to the hardening of the adhesive, positioning the traction pad in the position and at the location required at the surface of the coating, while exerting a sufficient pressure to have the adhesive flux;

c) waiting for the hardening of the adhesive;

d) cutting a notch in the coating at the periphery of the traction pad;

said method being characterised in that:

e) the pad complies with one of claims 1 to 13;

f) the pressure exerted at step b) is sufficient to bring the spacing means to rest on the surface of the coating;

g) the adhesive in excess, if any, which forms a curl at the surface of the coating around the traction pad, is eliminated between steps b) and c) prior to the hardening of the adhesive, and while holding the traction pad with a sufficient pressure to avoid any motion of the traction pad during the operation of elimination of the adhesive in excess in order to prevent any formation of a curl of hardened adhesive;

BRIEF DESCRIPTION OF THE DRAWINGS

FIGS. 4a and 4b show a traction pad according to the disclosed embodiments using a border.

FIGS. 5a and 5b show a traction pad according to the disclosed embodiments using spacers.

DETAILED DESCRIPTION

Figure 1:
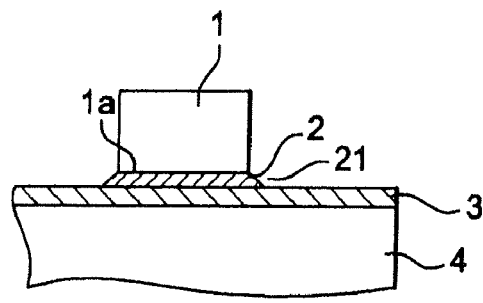
FIGS. 1 to 3 show the steps of the positioning of a traction pad in a known manner.
Figure 2:
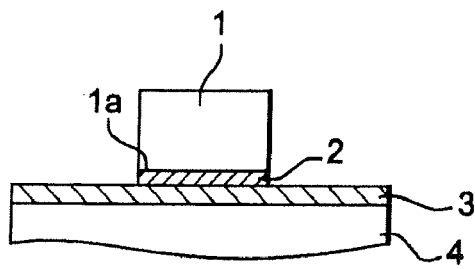
Figure 3:
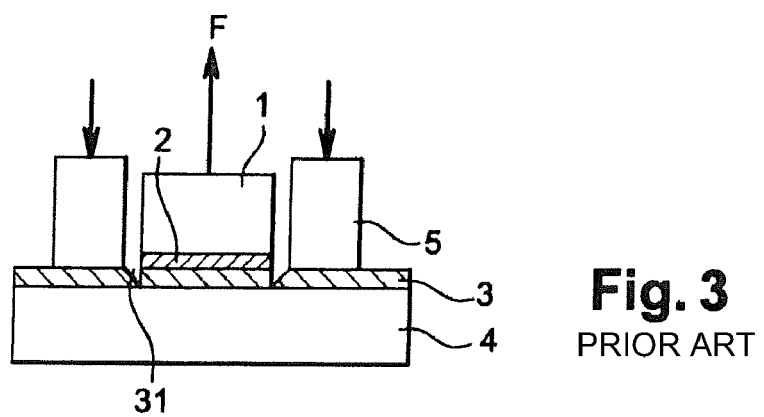

The present description and the drawings show a traction pad having an essentially axisymmetric shape. Such global shape of a traction pad is more or less generalized, because it is easy to make and it is described in the standard ISO 4624, but the disclosed embodiments can be applied to any shape of traction pad intended to be bonded either on a coating applied on a substrate for adhesion tests or directly on a material for surface cohesion tests.

At its base, a traction pad 1 includes a surface 1a intended to be bonded on a coating 3 covering a substrate 4, using an adhesive 2.

In order to apply traction efforts F on a surface of the coating 3, the dimension of which is accurately determined, the coating 3 is cut on the perimeter of the pad 1 with a notch 31. The aim of such notch is that the traction F can be uniformly applied on the surface of the coating 3 to be tested while avoiding that the coating 3, out of the bonded area which is determined by the surface 1a of the bonding of the traction pad 1, interferes with the result of the measurement, since the means 5 resting around the traction plot 1 are generally used to apply stresses in reaction to the traction force F applied to the test portion 4.

In order to avoid that the axis 20 of the traction pad 1 when in bonded position deviates from the normal to the surface of the coating 3, a counterbore 11 is made on the lower surface of the traction pad 1 while keeping the spacing elements 12, 13 from the bottom of the counterbore 11a with respect to the positioning plan and in such a way that the requested thickness of adhesive 2 is kept between the traction pad 1 and the coating 3. The dimensions and the disposition of said spacing means 12, 13 are selected so as to provide the traction pad 1 with a support surface which comes in contact with the free surface of the coating 3 in a stable and perpendicular way, with respect to axis 20 of the traction pad 1.

In one embodiment shown in FIGS. 4a and 4b, the spacing element has the shape of a continuous lip 12 which preferably follows the perimeter of the lower surface 1a of the traction pad 1. Preferably, such lip 12 is made as thin as possible so that the difference in surface between the bonded surface, i.e. the surface defined by the mark of the traction pad 1 minus the surface of the mark of the lip 12 on the surface of the coating 3, and the cut surface of the coating 3, i.e. the surface defined by the mark of the traction pad 1 is as little as possible so as not to interfere with the traction measurement.

For example, manufacturing a peripheral lip 12 in the shape of a web, 0.5 mm in thickness, is no technical problem for a traction pad 1 made of an aluminium alloy or steel which means a reduction in the surface of the bonding by 0.25% for a traction pad 1, 20 mm in diameter complying with standard ISO 4624. Such a deviation is perfectly negligible with respect to the dispersions of the measurements, which are established in such type of tests and can be taken into account in the calculations.

The spacing elements can also have the shape of spacers 13, as shown in FIGS. 5a and 5b, the height of which provides the requested thickness of adhesive 2. The spacers 13 will be at least three, not aligned and advantageously as spaced as possible, so that the support surface of the traction pad 1 is perfectly stable. A greater number of spacers 13 can be used and their shape has little importance, as long as the surface they occupy on the coating 3 remains negligible with respect to the surface of the bonding of the traction pad 1.

Whether the spacing elements are made with a lip 12, with spacers 13, or any other equivalent means, it is essential for the support surface defined by the lower surfaces of such spacing elements to be perfectly stable and perpendicular to the axis 20 of the traction pad 1, which corresponds to the direction of traction during the test proper. Such a quality is easily obtained when the spacing elements 12, 13 are made while leaving the corresponding material of the traction pad 1 upon the manufacturing of the counterbore 11, for example, by machining.

The bottom 11a of the counterbore 11 is substantially parallel to the support surface to obtain a homogeneous adhesive film with a substantially constant thickness. However, the unevenness of the surface of the bottom 11a of the counterbore 11, for example, scratches left by the passage of tools during the machining of the counterbore 11, will advantageously be kept or created to improve the qualities of adhesion of the adhesive on the traction pad 1, the connection between the pad 1 and the adhesive 2 having to be more resistant than the connection to be tested between the coating 3 and the substrate 4.

The traction pad 1 can further be equipped with means for facilitating the evacuation of the adhesive 2 in excess during the bonding operation of said pad 1 on the test-portion when the adhesive 2 is still fluid.

Figure 6:
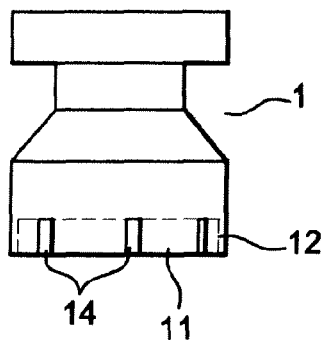
FIG. 6 shows a traction pad according to the disclosed embodiments using a border having interruptions.

Thus, the lip 12, as shown in FIG. 6, can be interrupted by free passages 14 on a portion of its length and on the whole or a part of its height, at one or more locations.

Figure 7:
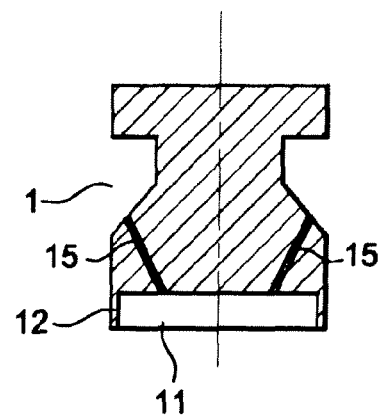
FIG. 7 shows a traction pad according to the disclosed embodiments with side exhaust stacks.
Figure 8:
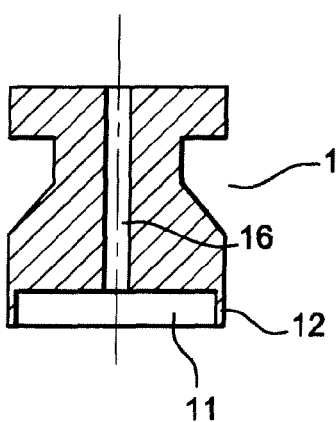
FIG. 8 shows a traction pad according to the disclosed embodiments with a vertical exhaust stack.
Figure 9:
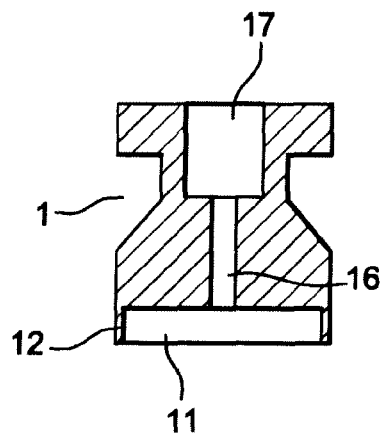
FIG. 9 shows a traction pad according to the disclosed embodiments, the exhaust stack of which includes an expansion chamber.

In other embodiments, as shown in FIGS. 7, 8 and 9, such means can have the shape of one or more exhaust stacks 15, 16 which can be through-holes or not, which in their lower parts are opened in the space defined by the inside of the peripheral lip 12, the bottom 11a of the counterbore 11 and the support surface of the traction pad 1.

The exhaust stacks 15, 16 can open onto the outside of the traction pad 1, the top of the traction pad 1, or the side wall of said pad.

When the exhaust stacks 15, 16 are not through-holes (these solutions are not shown in the drawings), attention should be paid for giving them a sufficient volume so that they can contain the adhesive which can flux into said exhaust stacks 15, 16 without the air trapped between the adhesive 2 and the blind bottom of the exhaust stacks 15, 16 to interfere with the up-going of the adhesive 2 into the stacks 15, 16.

In addition, an expansion chamber 17 can be provided to collect a more important quantity of adhesive 2 in excess, without the latter overflowing the traction pad 1 through the end of the exhaust stacks 15, 16 when these are through-holes.

Figure 10:
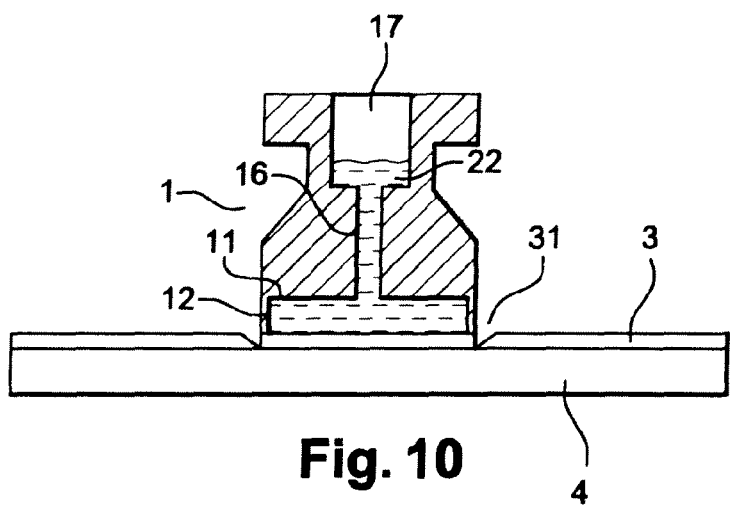
FIG. 10 shows a traction pad bonded to a coating to be tested.

As shown in FIG. 10, when the traction pad 1 and the coating to be tested 3 are bonded with the adhesive 2, the traction pad 1 is applied onto the coating to be tested 3 with a pressure which is sufficient to have the adhesive 2 in excess flux out while it is still fluid.

The adhesive 2 fluxing out through the edges of the traction pad 1 can easily be wiped before it dries without affecting the position of the traction pad 1, which can be held in its position during such operation using a moderate effort, thanks to the stability given by the support surface of the spacing means 12, 13. The curl of the not-hardened adhesive 21 is thus easily eliminated and the notch 31 can be made in the coating 3 to be tested very easily, when the adhesive has hardened.

When the traction pad 1 is provided with exhaust stacks 15, 16, the up-going of the adhesive 22 into the stacks 15, 16 and into the expansion chambers 17, if any, prevents or at least limits the need for eliminating the adhesive 2 fluxing out through the lower edge of the traction pad 1.

Tests carried out according to the standard ISO 4624 with traction pads complying with the disclosed embodiments, including a continuous peripheral lip 12 and a vertical exhaust stack 16 showed that less than ten tests suffice to obtain a reliable value of the tearing force F of the coating 3 tested, when over ninety tests were required with the prior art traction pads to obtain an equivalent reliability of measurement.

The invention claimed is:

1. In a device for measuring the adhesive quality of a coating using a coating adhesion test traction pad, the improvement comprising a coating adhesion test traction pad comprising:
   a lower bonding surface to be bonded on a surface of the coating prior to testing using an adhesive and defining a plane orthogonal to a reference traction axis of the coating adhesion test traction pad;
   a counterbored recess in the lower bonding surface, the counterbored recess having a substantially constant depth;
   spacing means between the lower bonding surface and a bottom of the counterbored recess, the spacing means having a height corresponding to a thickness of an adhesive to be provided between the coating adhesion test traction pad and the surface of the coating to be tested, the spacing means comprising a material similar to a material of the coating adhesion test traction pad; and
   at least an adhesive evacuation opening to let excess adhesive flux out of a bonding area defined by a mark of the traction pad on the surface of the coating, the at least one adhesive evacuation opening comprising one or more exhaust stacks extending into a body of the coating adhesion test traction pad.

2. A coating adhesion test traction pad according to claim 1, wherein the spacing means comprise a border at the lower bonding surface of the coating adhesion test traction pad.

3. A coating adhesion test traction pad according to claim 1, wherein the spacing means comprise wedges distributed at the lower bonding surface of the coating adhesion test traction pad.

4. A coating adhesion test traction pad according to claim 1, wherein the spacing means are located on a periphery of the lower bonding surface of the coating adhesion test traction pad.

5. A coating adhesion test traction pad according to claim 1, wherein the spacing means are obtained by leaving material from the traction pad upon making the counterbored recess.

6. A coating adhesion test traction pad according to claim 1, wherein the adhesive evacuation opening comprises one or more free passages provided in a border of the lower bonding surface of the coating adhesion test traction pad.

7. A coating adhesion test traction pad according to claim 1, wherein the adhesive evacuation opening comprises one or more free passages in the spacing means.

8. A coating adhesion test traction pad according to claim 1, wherein at least one of the exhaust stacks opens onto an outer surface of the coating adhesion test traction pad, in a part of said pad located above the bottom of the counterbored recess.

9. A coating adhesion test traction pad according to claim 1, wherein at least one of the exhaust stacks opens onto an expansion chamber.

10. A coating adhesion test traction pad according to claim 1, wherein the bottom of the counterbored recess includes a surface unevenness capable of improving the adhesion of the adhesive.

11. A method for bonding the traction pad of claim 1 on a coating covering a substrate using an adhesive, comprising:

applying the adhesive on a lower bonding surface of the coating adhesion test traction pad and/or on a surface of the coating;

prior to the hardening of the adhesive, positioning the coating adhesion test traction pad in a position and at a location requested at the surface of the coating by exerting a sufficient pressure to have the adhesive flux;

waiting for a hardening of the adhesive;

making a notch in the coating at a periphery of the traction pad; wherein:

the pressure exerted prior to the hardening of the adhesive is sufficient to bring the spacing means to rest on the surface of the coating and make the adhesive flux by adhesive evacuation openings;

the adhesive in excess, which form a curl at the surface of the coating around the traction pad are eliminated prior to the hardening of the adhesive and by holding the traction pad with a sufficient pressure to avoid any motion of the traction pad during the operation of the elimination of the adhesive in excess in order to prevent the formation of a curl of hardened adhesive.

\* \* \* \* \*